United States Patent [19]
Jones et al.

[11] Patent Number: 5,160,578
[45] Date of Patent: Nov. 3, 1992

[54] SEPARATING OF FIBERS FROM A FIBER-CONTAINING SOLID SAMPLE

[75] Inventors: Ronald D. Jones; Joseph B. Cross, both of Bartlesville, Okla.

[73] Assignee: Phillips Petroleum Company, Bartlesville, Okla.

[21] Appl. No.: 513,397

[22] Filed: Apr. 23, 1990

[51] Int. Cl.$^5$ ............................................. G01N 1/10
[52] U.S. Cl. ..................................... 156/655; 436/174; 436/175; 436/178; 162/55; 422/102
[58] Field of Search ........................ 156/655; 422/102; 436/178, 174, 175; 203/DIG. 2; D24/117; 162/55, 251, 189, 76, 56

[56] References Cited

U.S. PATENT DOCUMENTS

| | | | |
|---|---|---|---|
| 43,015 | 6/1864 | Fuller et al. | 162/56 |
| 4,517,053 | 5/1985 | Devine | 162/251 |
| 4,533,643 | 8/1985 | Bell et al. | 436/178 |
| 4,578,764 | 3/1986 | Hutchins et al. | 364/513 |
| 4,726,732 | 2/1988 | Kato | 414/744 |
| 4,727,494 | 2/1988 | Buote | 364/513 |
| 4,908,099 | 3/1990 | Delong | 162/78 X |

*Primary Examiner*—Thi Dang
*Attorney, Agent, or Firm*—William R. Sharp

[57] ABSTRACT

A method is provided for separating fibers from a solid sample which includes a solid material having fibers embedded therein. A first chamber, containing the sample, and a second chamber are defined within an appropriate vessel(s) such that the first chamber is positioned generally above the second chamber, and a filter is positioned between the chambers. At least one conduit, having at least one valve associated therewith, is further provided which is in fluid communication with the second chamber. Closure of such valve(s) substantially seals the second chamber except for fluid communication of the second chamber with the first chamber through the filter. While the second chamber is in such a sealed condition, digestion liquid is introduced to the first chamber so as to at least partially immerse the sample, whereupon liquid flows through the filter and into the second chamber so as to progressively increase the gas pressure in the second chamber to thereby progressively decrease the flow of liquid into the second chamber. After a predetermined digestion period, the valve(s) is opened to allow withdrawal of gases from the second chamber to thereby reduce the pressure therein and allow liquid remaining in the first chamber to flow into the second chamber.

11 Claims, 3 Drawing Sheets

```
┌─────────────────────────────────────────────────┐
│  AT LEAST PARTIALLY FILL CHAMBER 44 WITH DIGESTION │
│  LIQUID (I.E. NITRIC ACID) SO AS TO IMMERSE SAMPLE 47│
│  (I.E. SOLID MATERIAL SUCH AS POLY(PHENYLENE SULFIDE)│
│  HAVING CARBON FIBERS EMBEDDED THEREIN) IN DIGESTION │
│  LIQUID; DIGESTION LIQUID BEING CAPABLE OF DISSOLVING│
│     ONLY SOLID MATERIAL OF SAMPLE TO LIQUID FORM.    │
└─────────────────────────────────────────────────┘
                        │
                        ▼
┌─────────────────────────────────────────────────┐
│          MAINTAIN EACH VALVE IN CLOSED POSITION      │
│            FOR A PREDETERMINED DIGESTION PERIOD,     │
│        WHEREIN DURING A PORTION OF DIGESTION PERIOD  │
│       LIQUID FLOWS FROM CHAMBER 44 AND THROUGH FILTER 42│
│           INTO CHAMBER 30 UNTIL SUCH FLOW SUBSTANTIALLY│
│         TERMINATES, AND FURTHER WHEREIN VESSEL 34 AND ITS│
│           CONTENTS ARE HEATED DURING AT LEAST THIS STEP.│
└─────────────────────────────────────────────────┘
                        │
                        ▼
┌─────────────────────────────────────────────────┐
│              OPEN VALVE 58, LEAVING VALVES           │
│           64, 66, AND 68 IN CLOSED POSITIONS.        │
└─────────────────────────────────────────────────┘
                        │
                        ▼
┌─────────────────────────────────────────────────┐
│         DRAIN CHAMBER 44 BY ACTIVATING PUMP 56       │
│         TO WITHDRAW GASES FROM CHAMBER 30 AND REDUCE │
│           GAS PRESSURE THEREIN SO THAT LIQUID REMAINING│
│       IN CHAMBER 44 AFTER DIGESTION PERIOD FLOWS THROUGH│
│         FILTER 42 AND INTO CHAMBER 30, WHEREIN THE FIBERS│
│           REMAIN IN CHAMBER 44 AT COMPLETION OF THIS STEP.│
└─────────────────────────────────────────────────┘
                        │
                        ▼
┌─────────────────────────────────────────────────┐
│      CLOSE VALVE 58 AND OPEN VALVES 64, 66 AND 68.   │
└─────────────────────────────────────────────────┘
                        │
                        ▼
┌─────────────────────────────────────────────────┐
│      DRAIN CHAMBER 30 INTO WASTE TANK BY ACTIVATING  │
│          PUMP 56 TO WITHDRAW GASES FROM WASTE TANK   │
│       AND REDUCE GAS PRESSURE THEREIN, THEREBY RESULTING│
│          IN FLOW OF LIQUID FROM CHAMBER 30 TO WASTE TANK.│
└─────────────────────────────────────────────────┘
```

*FIG. 4*

SEPARATING OF FIBERS FROM A FIBER-CONTAINING SOLID SAMPLE

BACKGROUND OF THE INVENTION

This invention relates to an apparatus and method for separating fibers from a solid sample which comprises a solid material having such fibers embedded therein. Such a solid sample is commonly characterized as a "composite".

Fiber content plays a major role in determining the structural characteristics of composites. Therefore, it is frequently desirable to determine the fiber content of a composite which is being manufactured and/or tested. In order to determine the fiber content of such a composite, it is necessary to separate the fibers from a composite sample for weighing. Heretofore, such separation techniques have been labor intensive and potentially hazardous to laboratory personnel.

By way of example, carbon fibers are typically separated from poly(phenylene sulfide) based composites by utilizing nitric acid to digest or dissolve the solid poly(phenylene sulfide) resin to liquid form. According to such a technique, a quantity of nitric acid is poured into a beaker, the beaker placed on a hot plate, and the acid's temperature raised to about 100° C. At such time a composite sample is placed in the acid and allowed to digest for a predetermined period of time, after which the beaker's liquid contents are poured into a buchner funnel (which contains an appropriate filter) while carefully holding back the carbon fibers with a glass rod. Additional nitric acid is then added to the beaker and the beaker is returned to the hot plate for a second digestion period to dissolve any residual resin. The contents of the beaker are again poured into the buchner funnel, this time along with the carbon fibers. The filter in the buchner funnel allows passage of liquids therethrough but retains the carbon fibers. All of the above-described steps are performed manually so as to risk exposure to hot acid, acid fumes, and airborne fibers.

SUMMARY OF THE INVENTION

It is, therefore, an object of the invention to provide an apparatus and method of separating fibers from a solid sample comprising a solid material and fibers embedded therein, wherein such apparatus and method are adaptable to fully automated operation.

The above object is realized by an apparatus which comprises: a vessel means having an upper end, a lower end, and an interior surface which defines therein a first chamber, for receiving the sample, and also a second chamber, wherein the first chamber is positioned generally above the second chamber; a filter means mounted within the vessel means between the first and second chambers so as to extend across the interior of the vessel means such that the filter means contacts the interior surface of the vessel means around the circumference of the filter means, the filter means being adapted to provide fluid communication therethrough between the first and second chambers and being further adapted to receive liquid but not fibers therethrough; means for introducing a digestion liquid into the first chamber, the digestion liquid being capable of dissolving only the solid material of the sample to liquid form; means for withdrawing gas from the second chamber; a conduit means having an open end in fluid communication with the second chamber at a position above the lower end of the vessel means, the conduit means extending from said open end thereof to the withdrawing means; a valve means associated with the conduit means for providing selective fluid communication between the second chamber and the withdrawing means, wherein the valve means has an open position which allows fluid communication between the second chamber and the withdrawing means and a closed position in which the second chamber is substantially sealable except for fluid communication with the first chamber through the filter means.

According to another aspect of the invention, there is provided a method which employs certain aspects of the above-described apparatus and which comprises the steps of: at least partially filling the first chamber with a digestion liquid so as to at least partially immerse the sample in the digestion liquid; maintaining the valve means in a closed position for a predetermined period of time after the completion of the filling step so as to substantially seal the second chamber except for fluid communication with the first chamber through the filter means, wherein during at least a portion of such period of time liquid flows from the first chamber and through the filter means into the second chamber so as to progressively increase the gas pressure within the second chamber to thereby progressively decrease the flow of liquid into the second chamber, and further wherein at the completion of this step the liquid level in the second chamber is below the position of the open end of the first conduit means; opening the valve means immediately after the valve means has been closed for said predetermined period of time; withdrawing at least a portion of the gaseous contents of the second chamber through the conduit means and the valve means so as to reduce the gas pressure in the second chamber sufficiently so that a substantial portion of liquid remaining in the first chamber flows through the filter means and into the second chamber.

The above described vessel means in accordance with the invention serves a dual function; that is, it provides the chamber (first chamber) in which the sample is digested and it also has the capability of separating the resulting liquid from the fibers. This avoids the step of pouring the liquid and fiber mixture from one container in which digestion takes place to another container in which filtration takes place. Therefore, the invention is particularly adaptable to automated operation in accordance with a preferred embodiment of the invention wherein valves are operated in response to commands from a computer. In such a preferred embodiment which is described herein, the vessel means includes a first vessel, having the first chamber therein, and a second vessel having the second chamber therein and upon which the first vessel can be positioned by a robot. The robot can also be employed to position over the first chamber a nozzle from which the digestion liquid is released.

BRIEF DESCRIPTION OF THE DRAWINGS

FIG. 4 is a flow chart which sets forth the various steps of a method in accordance with a preferred embodiment of the invention and using the apparatus of FIGS. 1-3.

DETAILED DESCRIPTION OF THE INVENTION

Figure 1:
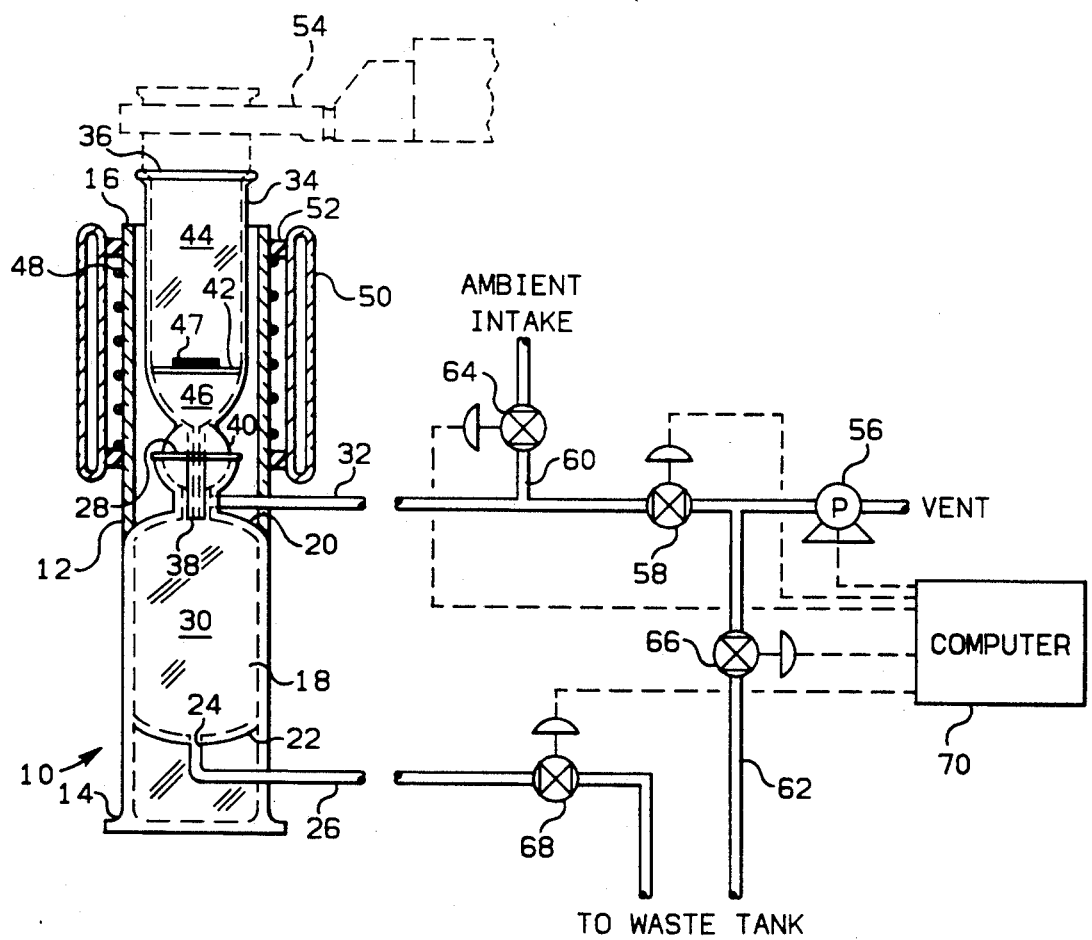
FIG. 1 is a partial cross sectional view of one embodiment of an apparatus in accordance with the invention, wherein a first vessel is shown as being positioned upon a second vessel by a robot arm.

Referring to FIG. 1, the illustrated apparatus includes a generally cylindrical member 10 which comprises a sidewall 12. Sidewall 12 extends from a lower end 14, having a supportive base connected thereto, to an upper open end 16.

A lower portion of sidewall 12 functions as the sidewall of a vessel 18 which also includes walls 20 and 22 radially extending from the interior surface of sidewall 12. Wall 22 defines the lower end 24 of vessel 18 which communicates with a conduit 26. As shown, conduit 26 extends through sidewall 12 to the exterior of cylindrical member 10. Vessel 18 further includes an upper mouth portion which defines the upper open end 28 of vessel 18. A chamber 30 is accordingly defined within vessel 18 by its interior surface (represented by dashed lines) which extends between lower end 24 and upper end 28 and which communicates with an open end of a conduit 32 at a position above lower end 24 and preferably near upper end 28. Further as shown, conduit 32 extends through sidewall 12 and to the exterior of cylindrical member 10.

The apparatus of FIG. 1 further includes a vessel 34 having an upper open end 36 and a lower open end 38. As shown, vessel 34 is generally funnel-shaped so as to converge from a larger upper diameter to a smaller diameter near lower open end 38. Vessel 34 has associated therewith a ball joint 40, preferably composed of ground glass, which is adapted to set in sealing engagement upon upper end 28 of vessel 18.

A filter 42 is further provided which is mounted within vessel 34 so as to extend across the interior thereof and divide the interior of vessel 34 into two chambers, denoted as chambers 44 and 46. As shown, chambers 44 and 46 are defined by the respective upper and lower opposing surfaces of filter 42 in conjunction with the interior surface (represented by dashed lines) of vessel 34. Chamber 44 is positioned above chamber 30 and extends from upper open end 36 to the upper surface of filter 42. Chamber 46 extends from the lower opposing surface of filter 42 to lower open end 38. Lower open end 38 is positioned such that chamber 46 communicates with chamber 30 through lower open end 38.

Filter 42 provides fluid communication therethrough between chambers 44 and 46 and further is adapted to receive liquid but not fibers therethrough. A particularly suitable filter for most applications comprises fritted glass. However, it is within the scope of broad aspects of the invention to employ any type of filter capable of performing the desired filtering function in the digestion environment.

A solid sample 47 is shown in FIG. 1 as resting upon the upper surface of filter 42. Sample 47 is a composite which comprises a solid material having fibers embedded therein. One example of such a sample includes a poly(arylene sulfide) such as poly(phenylene sulfide) as the solid material and carbon or glass fibers.

Means for heating vessel 34 and its contents is provided by a coil of wire (i.e. nichrome), shown in cross section at 48, which is wrapped around the exterior surface of an upper portion of sidewall 12. Leads, not shown, can be connected to a suitable electrical power source. A suitable temperature controller, not shown, can be employed to regulate the temperature of coil 48.

A generally annular collar 50 is positioned so as to surround sidewall 12 and coil 48. Collar 50 is preferably hollow and evacuated so as to function as a thermal insulator in preventing heat loss. Collar 50 is preferably connected to the exterior surface of sidewall 12 by means of annular sealant rings 52 at the upper and lower ends of collar 50. Sealant rings 52, which can be composed of a suitable sealant such as silicone rubber, further function in conjunction with collar 50 to protect coil 48 from digestion liquid fumes.

With respect to materials of various components of the apparatus described above, including cylindrical member 10, vessel 18, vessel 34 and collar 50, it is preferable to use materials which are compatible with and resistant to the digestion liquid employed. For example, where the digestion liquid is nitric acid, it is preferable that the listed components of the apparatus be composed of a glass, such as Pyrex.

As shown in dashed lines, vessel 34 can be positioned within cylindrical member 10 and upon vessel 18 or removed from such a position by a suitable robot arm 54. Robot arm 54 comprises a pair of elongated members, only one of which is shown, which clamp around the exterior surface of vessel 34. A suitable robot for use with the present invention is a Zymate robot as manufactured by Zymark Corporation.

The apparatus further includes a series of valves, more specifically described below, which operate in conjunction with a pump 56 to control the flow of liquid through vessels 18 and 34. Pump 56 is preferably a bellows pump, but can be any other suitable means of withdrawing gas from chamber 30, such as a water aspirator. As shown, conduit 32 extends between chamber 30 and pump 56. Valve 58 is positioned along conduit 32 so as to provide selective fluid communication between chamber 30 and pump 56. Conduits 60 and 62 branch from conduit 32 and have associated therewith valves 64 and 66, respectively. Conduit 60 is in selective communication with the ambient atmosphere through valve 64 so as to serve as an ambient intake as further discussed below. Conduit 62 extends to a waste tank. Conduit 26 extends between lower open end 24 of vessel 18 and the waste tank, and has associated therewith a valve 68 which provides selective communication between chamber 30 and the waste tank.

The above discussed valves are preferably solenoid valves which are automatically controllable by means of an appropriately programmed computer 70. Signals from computer 70, converted from digital to analog form, can be transmitted to the valves via electrical signal lines which in FIG. 1 are shown as dashed lines extending between the computer and the respective valves. Pump 56 is further automatically controllable by a suitable electrical signal line from computer 70. Although not shown, computer 70 can also be employed to control robot arm 54 by means of an electrical signal line to the motor which controls the robot arm.

Figure 2:
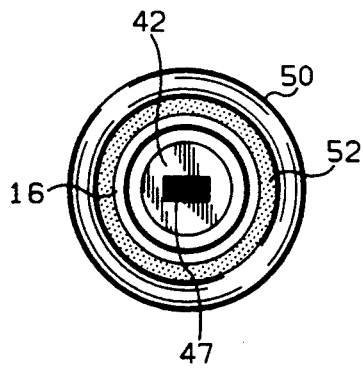
FIG. 2 is an elevational view of the apparatus of FIG. 1 which shows the manner in which a filter is mounted in the first vessel.

Referring now to FIG. 2, there is shown an elevational view of the FIG. 1 apparatus which shows the upper end of collar 50, upper annular sealant ring 52, upper end 16 of cylindrical member 10, sample 47, and filter 42. This FIGURE shows filter 42 to be mounted within vessel 34 such that it contacts the interior surface of vessel 34 around the circumference of filter 42.

Figure 3:
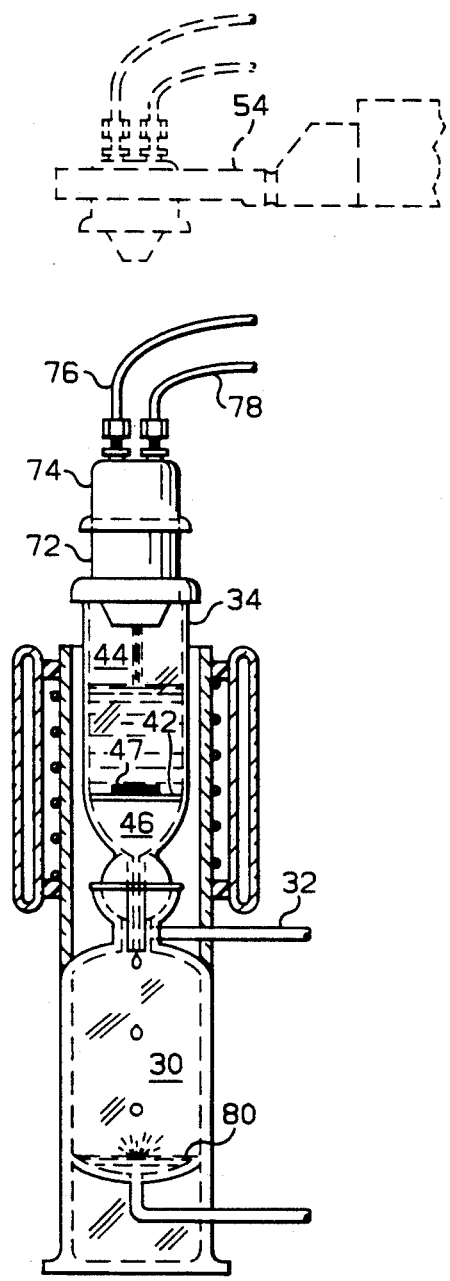
FIG. 3 shows the apparatus of FIG. 1 at a later stage of the method disclosed herein wherein a nozzle is positioned by the robot arm to release digestion liquid into the first vessel.

Referring now to FIG. 3, the apparatus as illustrated in FIGS. 1 and 2 is shown at a later stage of a method in accordance with the invention and as is later described in detail. A vessel cover 72 is shown as positioned upon the upper end of vessel 34 and can be so positioned by robot arm 54. Vessel cover 72 functions to promote refluxing during the digestion process and further functions as a holder for a nozzle 74 which is adapted to set upon vessel cover 72. Two supply conduits, 76 and 78, are connected to nozzle 74 in the illustrated embodiment. One supply conduit can supply digestion liquid whereas the other supply conduit can supply water for the purpose of washing vessel 34 as will be discussed in more detail below. In a similar manner to the positioning of vessel 34 in FIG. 1, nozzle 74, as shown in dashed lines, can be lowered into or removed from its operating position upon vessel cover 72 by robot arm 54.

A preferred embodiment of a method in accordance with the invention will now be described with reference to the FIGURES.

As shown in FIG. 1, robot arm 54 positions vessel 34 upon vessel 18. This is carried out after vessel 34 has been removed from an appropriate storage environment, such as for example a partially evacuated desiccator, where the vessel is kept clean and dry. Such removal of vessel 34 from a desiccator, as well as introduction of sample 47 to vessel 34, can also be carried out with robot arm 54.

After having placed vessel cover 72 upon vessel 34, robot arm 54 positions nozzle 74 upon vessel cover 72 as shown in FIG. 3 for the purpose of introducing digestion liquid to chamber 44 of vessel 34.

The digestion liquid is preferably capable of dissolving only the solid material of sample 47 to liquid form. Therefore, the digestion liquid functions to selectively digest only the solid material of sample 47 and not the fibers embedded therein. One example of a digestion liquid is nitric acid, which is particularly suitable in digestion of a sample which comprises poly(phenylene sulfide) and carbon fibers.

At this point of the method, each of valves 58, 64, 66 and 68 are closed so as to seal chamber 30 except for fluid communication with chamber 44 through chamber 46 and filter 42. Each of these valves will be maintained in their respective closed positions during the steps described below until indicated otherwise. It is generally preferred that all valves be maintained in the closed position during introduction of digestion liquid and digestion of sample 47.

As shown in FIG. 3, digestion liquid is released from nozzle 72 so as to at least partially fill chamber 44 and immerse sample 47 in digestion liquid. Immediately after this step is completed, a suitable timer is set by computer 70. This timer, which can then be incorporated into the hardware of computer 70, is set for the desired and predetermined time of digestion, hereinafter referred as to the digestion period.

Liquid steadily drips through filter 42, into and through chamber 46, and finally into chamber 30. Accordingly, liquid collects in chamber 30 during which the gas pressure within chamber 30 progressively increases to thereby progressively decrease the flow of liquid into chamber 30. Typically, the above-mentioned digestion period is sufficiently long such that gas pressure in chamber 30 substantially terminates (to perhaps an occasional drip) the flow of liquid into chamber 30 before the end of the digestion period. This condition occurs when an equilibrium condition is reached between the weight of liquid in chamber 44 and the gas pressure in chamber 30.

During the digestion period, at least a portion of the solid material of sample 47 is dissolved to liquid form so as to flow through filter 42 and into chamber 30. It is desirable that the digestion period, size of sample 47, and amount of digestion liquid employed be selected so that the level of liquid in chamber 30 at the completion of the digestion period is below the open end of conduit 32 which communicates with the chamber 30, such as, for example, the level indicated at 80 in FIG. 3. This prevents backup of liquid into conduit 32.

It is further preferable that vessel 34 and its contents is heated by coil 48 during the digestion period. Such heating promotes the digestion process and thereby shortens the necessary length of the digestion period. In the particular embodiment wherein nitric acid is employed to digest a poly(arylene sulfide) based sample, it is preferred to heat the wire of coil 48 to about 150° C. so that the nitric acid in vessel 34 is maintained at a temperature of about 100° C. to about 130° C.

Immediately after the completion of the digestion period, valve 58 is opened in response to an appropriate signal transmitted from computer 70, thereby providing fluid communication between chamber 30 and pump 56. Pump 56 is then activated by an appropriate signal from computer 70 so as to withdraw gases from chamber 30. Such gases, which include primarily air and fumes from the digestion process, pass through conduit 32 and valve 58, and are vented from the outlet of pump 56. In accordance with the invention, gases are withdrawn from chamber 30 until the gas pressure in chamber 30 is reduced sufficiently to cause flow of liquid from chamber 44 and into chamber 30. Typically, a reduction in gas pressure of about 3 to about 5 psi is sufficient for this purpose, assuming that the gas pressure in chamber 44 is atmospheric pressure.

After draining of liquid from chamber 44 into chamber 30, valve 58 is closed and valves 64, 66 and 68 are opened in response to appropriate signal commands from computer 70. In addition, pump 56 is again activated so as to withdraw gases from the waste tank through conduit 62. This reduces the gas pressure in the waste tank, whereas the gas pressure above collected liquid in chamber 30 is increased in response to the flow of ambient air into chamber 30 via conduit 32 and valve 64. This condition results in flow of liquid from chamber 30 and into the waste tank via conduit 26 and valve 68.

If desired, the above series of steps can be repeated to dissolve any solid material remaining in chamber 44.

Only fibers from sample 47 now remain upon the upper surface of filter 42. It is preferably at this point to wash vessel 34 by releasing water from nozzle 74 into chamber 44, followed by draining of chambers 44 and 30 by the procedure described above. After washing, it is further preferable to dry vessel 34 by continued heating thereof to thereby evaporate water adhering to the interior surface of vessel 34. Vessel 34 can now be removed from its position upon vessel 18, after removal of nozzle 74 and vessel cover 72, by robot arm 54 by withdrawing vessel 34 from cylindrical member 10 in an upward motion.

FIG. 4 illustrates the various steps of the preferred embodiment described above.

Where the method is employed in conjunction with a determination of fiber content of sample 47, robot arm 54 can be employed to appropriately manipulate vessel 34 in making the following weight measurements, from which the fiber content can be determined: (1) weight of empty vessel 34; (2) weight of vessel 34 having the undigested sample therein; and (3) weight of vessel 34 having only the fibers therein after digestion.

Thus, there is provided by the invention an apparatus and method for separating fibers from a fiber-containing solid sample which are particularly adapted to automated operation. Such automated operation avoids manual manipulation of the digestion liquid, sample, etc. which can be dangerous and time consuming.

Obviously many modifications and variations of the present invention are possible in light of the above teachings. It is therefore to be understood that within the scope of the appeneded claims the invention may be practiced otherwise than as specifically described.

That which is claimed is:

1. A method for separating fibers from a solid sample which comprises a solid material having fibers embedded therein, said method comprising:
   (a) providing a first vessel having an interior surface and a filter means with opposing surfaces mounted therein so as to extend across the interior of said first vessel such that said filter means contacts said interior surface around the circumference of said filter means, wherein a first chamber for receiving said sample is defined within said first vessel by said interior surface and one of the opposing surfaces of said filter means, and wherein said filter means is adapted to receive liquid but not fibers therethrough;
   (b) providing a second vessel having an interior surface defining a second chamber therein and also having an upper end and a lower end;
   (c) providing a first conduit means having an open end in fluid communication with said second chamber at a position above the lower end of said second vessel;
   (d) providing a first valve means associated with said first conduit means, wherein said first valve means has an open position and a closed position;
   (e) robotically positioning said first vessel upon the upper end of said second vessel so that said first chamber is positioned above said second chamber and so that said filter means is positioned between said first and second chambers to provide fluid communication through said filter means between said first and second chambers;
   (f) at least partially filling said first chamber with a digestion liquid so as to at least partially immerse said sample in said digestion liquid, said digestion liquid being capable of dissolving only said solid material of said sample to liquid form;
   (g) maintaining said first valve means in a closed position for a predetermined period of time after the completion of step (f) so as to substantially seal said second chamber except for fluid communication with said first chamber through said filter means, wherein during at least a portion of said period of time liquid flows from said first chamber and through said filter means into said second chamber so as to progressively increase the gas pressure within said second chamber to thereby progressively decrease the flow of liquid into said second chamber, and further wherein at the completion of this step the liquid level in said second chamber is below the position of the open end of said first conduit means;
   (h) opening said first valve means immediately after the completion of step (g);
   (i) withdrawing at least a portion of the gaseous contents of said second chamber through said first conduit means and said first valve means after step (h) so as to reduce the gas pressure in said second chamber sufficiently so that a substantial portion of liquid remaining in said first chamber after step (g) flows through said filter means and into said second chamber.

2. A method as recited in claim 1 wherein said period of time in step (g) is sufficient such that liquid flow into said chamber substantially terminates during step (g).

3. A method as recited in claim 2 further comprising heating said first chamber and its contents during at least step (g).

4. A method as recited in claim 3 wherein said lower end is open and wherein there is provided a waste tank, a second conduit means extending between said lower open end and said waste tank, and a second valve means associated with said second conduit means and having an open position and a closed position, wherein said second valve means is in the closed position during steps (f)–(i), said method further comprising opening said second valve means after step (i) to allow liquid to drain from said second chamber, through said second conduit means and into said waste tank.

5. A method as recited in claim 4 wherein in step (f) said digestion liquid is introduced into said first chamber by robotically positioning above said first chamber a nozzle from which digestion fluid is released.

6. A method as recited in claim 5 further comprising the step of robotically removing said first vessel from its position upon said second vessel after step (i).

7. A method as recited in claim 6 wherein said first and second valve means are operated in response to commands by a computer.

8. A method as recited in claim 7 wherein said solid material of said sample comprises a poly(arylene sulfide).

9. A method as recited in claim 8 wherein said solid material comprises poly(phenylene sulfide).

10. A method as recited in claim 9 wherein said fibers are selected from the group consisting of carbon fibers and glass fibers.

11. A method as recited in claim 10 wherein said digestion liquid comprises nitric acid.

* * * * *